United States Patent
Sheldon et al.

(10) Patent No.: US 9,937,352 B2
(45) Date of Patent: Apr. 10, 2018

(54) RATE RESPONSIVE CARDIAC PACING CONTROL USING POSTURE

(71) Applicant: Medtronic, Inc., Minneapolis, MN (US)

(72) Inventors: Todd J Sheldon, North Oaks, MN (US); Wade M Demmer, Coon Rapids, MN (US); Eric R Williams, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 14/920,228

(22) Filed: Oct. 22, 2015

(65) Prior Publication Data

US 2017/0113051 A1    Apr. 27, 2017

(51) Int. Cl.
| | | |
|---|---|---|
| *A61N 1/365* | (2006.01) | |
| *A61N 1/375* | (2006.01) | |
| *A61B 5/11* | (2006.01) | |
| *A61B 5/00* | (2006.01) | |
| *A61N 1/372* | (2006.01) | |

(52) U.S. Cl.
CPC ........ *A61N 1/36585* (2013.01); *A61B 5/1116* (2013.01); *A61B 5/4836* (2013.01); *A61N 1/36535* (2013.01); *A61N 1/36542* (2013.01); *A61N 1/3756* (2013.01); *A61N 1/37205* (2013.01); *A61B 5/1121* (2013.01)

(58) Field of Classification Search
USPC ...................................... 607/9, 18
See application file for complete search history.

(56) References Cited

U.S. PATENT DOCUMENTS

| | | |
|---|---|---|
| 761,162 A | 5/1904 | Gold |
| 4,374,382 A | 2/1983 | Markowitz |
| 4,476,868 A | 10/1984 | Thompson |

(Continued)

FOREIGN PATENT DOCUMENTS

| | | |
|---|---|---|
| CN | 1838076 A | 9/2006 |
| EP | 1 116 495 A2 | 7/2001 |

(Continued)

OTHER PUBLICATIONS

Demmer, et al., "Method and Apparatus for Detecting Loss of Capture", U.S. Appl. No. 14/261,776, filed Apr. 25, 2014, 44 pages.

(Continued)

*Primary Examiner* — Nicole F Johnson

(57) ABSTRACT

An implantable rate responsive pacemaker includes a sensor module configured to produce an activity signal correlated to a metabolic demand of a patient and a posture signal correlated to patient posture. The pacemaker further includes a pulse generator configured to generate and deliver pacing pulses to a patient's heart via a pair of electrodes coupled to the pacemaker. A control module is coupled to the pulse generator and the sensor module and is configured to determine a sensor indicated pacing rate from the activity signal, compare the posture signal to verification criteria for confirming an exercising posture of the patient, and withhold an adjustment of a pacing rate to the sensor indicated pacing rate responsive to the verification criteria not being met.

24 Claims, 7 Drawing Sheets

(56) References Cited

U.S. PATENT DOCUMENTS

| | | | |
|---|---|---|---|
| 4,485,813 A | 12/1984 | Anderson et al. | |
| 5,052,388 A | 10/1991 | Sivula et al. | |
| 5,074,302 A | 12/1991 | Poore et al. | |
| 5,117,824 A | 6/1992 | Keimel et al. | |
| 5,154,170 A | 10/1992 | Bennett et al. | |
| 5,165,404 A | 11/1992 | Andersson et al. | |
| 5,165,405 A | 11/1992 | Eckwall | |
| 5,172,690 A | 12/1992 | Nappholz et al. | |
| 5,190,034 A | 3/1993 | Sholder | |
| 5,222,493 A | 6/1993 | Sholder | |
| 5,226,413 A | 7/1993 | Bennett et al. | |
| 5,231,986 A | 8/1993 | Bennett | |
| 5,285,780 A | 2/1994 | Tsuji et al. | |
| 5,304,208 A | 4/1994 | Inguaggiato et al. | |
| 5,312,454 A | 5/1994 | Roline | |
| 5,320,643 A | 6/1994 | Roline et al. | |
| 5,324,310 A | 6/1994 | Greeninger et al. | |
| 5,345,362 A | 9/1994 | Winkler | |
| 5,354,317 A | 10/1994 | Alt | |
| 5,423,867 A | 6/1995 | Poore et al. | |
| 5,447,525 A | 9/1995 | Powell et al. | |
| 5,496,351 A | 3/1996 | Plicchi et al. | |
| 5,507,785 A | 4/1996 | Deno | |
| 5,562,711 A | 10/1996 | Yerich et al. | |
| 5,507,782 A | 12/1996 | Kieval | |
| 5,593,431 A | 1/1997 | Sheldon | |
| 5,601,615 A | 2/1997 | Markowitz et al. | |
| 5,609,612 A | 3/1997 | Plicchi et al. | |
| 5,628,777 A | 5/1997 | Moberg et al. | |
| 5,683,432 A | 11/1997 | Goedeke | |
| 5,693,075 A | 12/1997 | Plicchi et al. | |
| 5,720,769 A | 2/1998 | Van Oort | |
| 5,755,740 A | 5/1998 | Nappholz | |
| 5,766,230 A | 6/1998 | Routh et al. | |
| 5,782,889 A | 7/1998 | Högnelid et al. | |
| 5,944,745 A | 8/1999 | Rueter | |
| 5,954,755 A | 9/1999 | Casavant | |
| 6,044,297 A | 3/2000 | Sheldon et al. | |
| 6,389,316 B1 | 5/2002 | Bornzin et al. | |
| 6,449,508 B1 | 9/2002 | Sheldon et al. | |
| 6,553,259 B2 | 4/2003 | Mouchawar et al. | |
| 6,772,005 B2 | 8/2004 | Casavant et al. | |
| 6,819,955 B2 | 11/2004 | Levine | |
| 6,950,704 B1 | 9/2005 | Whitehurst | |
| 7,031,772 B2 | 4/2006 | Condie | |
| 7,076,283 B2 | 7/2006 | Cho et al. | |
| 7,130,690 B2 | 10/2006 | Rueter et al. | |
| 7,280,868 B2 | 10/2007 | Rueter et al. | |
| 7,400,924 B2 | 7/2008 | Rueter | |
| 7,457,666 B2 | 11/2008 | Bohn et al. | |
| 7,532,930 B2 | 5/2009 | Schermeier et al. | |
| 7,761,162 B2 | 7/2010 | Dong et al. | |
| 7,778,696 B2 | 8/2010 | Sathaye | |
| 7,783,355 B2 | 8/2010 | Rueter | |
| 7,818,059 B2 | 10/2010 | Rueter et al. | |
| 7,831,303 B2 | 11/2010 | Rueter et al. | |
| 8,280,509 B2 | 10/2012 | Sathaye | |
| 8,401,666 B2 | 3/2013 | Skelton et al. | |
| 8,433,409 B2 | 4/2013 | Johnson | |
| 8,532,785 B1 | 9/2013 | Crutchfield | |
| 8,541,131 B2 | 9/2013 | Lund | |
| 8,956,295 B2 | 2/2015 | Ni et al. | |
| 9,452,292 B2 | 9/2016 | Demmer et al. | |
| 2002/0183798 A1 | 12/2002 | Vonk | |
| 2003/0069611 A1 | 4/2003 | Levine | |
| 2003/0078624 A1 | 4/2003 | Carlson et al. | |
| 2003/0078627 A1 | 4/2003 | Casavant et al. | |
| 2003/0083700 A1 | 5/2003 | Hill | |
| 2003/0083712 A1 | 5/2003 | Rueter et al. | |
| 2003/0195579 A1 | 10/2003 | Bradley et al. | |
| 2003/0204214 A1 | 10/2003 | Ferek-Patric | |
| 2004/0030358 A1 | 2/2004 | Rueter et al. | |
| 2004/0088019 A1 | 5/2004 | Rueter et al. | |
| 2004/0260352 A1 | 12/2004 | Rueter et al. | |
| 2005/0015985 A1 | 1/2005 | Dvoskin | |
| 2005/0021095 A1 | 1/2005 | Rueter et al. | |
| 2005/0159785 A1 | 7/2005 | Rueter | |
| 2005/0222630 A1 | 10/2005 | Schermeier et al. | |
| 2006/0155338 A1 | 7/2006 | Mongeon et al. | |
| 2006/0241710 A1 | 10/2006 | Rueter | |
| 2006/0247705 A1 | 11/2006 | Rueter et al. | |
| 2006/0253156 A1* | 11/2006 | Pastore | A61N 1/365 607/9 |
| 2007/0115277 A1 | 5/2007 | Wang et al. | |
| 2008/0195165 A1* | 8/2008 | Stahmann | A61B 5/0215 607/18 |
| 2010/0010380 A1 | 1/2010 | Panken et al. | |
| 2010/0010583 A1 | 1/2010 | Panken et al. | |
| 2011/0012759 A1 | 1/2011 | Yin | |
| 2011/0029034 A1 | 2/2011 | Fischer et al. | |
| 2011/0152963 A1 | 6/2011 | Stahmann et al. | |
| 2012/0065524 A1 | 3/2012 | Morren et al. | |
| 2012/0109259 A1 | 5/2012 | Bond et al. | |
| 2012/0172892 A1 | 7/2012 | Grubac | |
| 2012/0245476 A1 | 9/2012 | Skerl et al. | |
| 2013/0035748 A1 | 2/2013 | Bonner | |
| 2013/0079861 A1 | 3/2013 | Reinert et al. | |
| 2013/0090702 A1 | 4/2013 | Mongeon et al. | |
| 2013/0116602 A1 | 5/2013 | Van Den Heuvel et al. | |
| 2013/0150911 A1 | 6/2013 | Perschbacher et al. | |
| 2013/0211205 A1 | 8/2013 | Havel et al. | |
| 2013/0289652 A1 | 10/2013 | Skelton et al. | |
| 2015/0173655 A1* | 6/2015 | Demmer | A61B 5/1118 600/595 |
| 2015/0217119 A1 | 8/2015 | Nikolski et al. | |
| 2015/0238769 A1 | 8/2015 | Demmer et al. | |
| 2016/0144191 A1 | 5/2016 | Sheldon et al. | |

FOREIGN PATENT DOCUMENTS

| | | |
|---|---|---|
| EP | 1116495 A2 | 7/2001 |
| EP | 2239007 A1 | 10/2010 |
| WO | 2004/041086 A1 | 5/2004 |

OTHER PUBLICATIONS (PCT/US2014/067337) PCT Notification of Transmittal of the International Search Report and the Written Opinion of the International Searching Authority.
(PCT/US2015/062137) Invitation to Pay Additional fees and, where applicable, protest fee, dated Mar. 1, 2016, 8 pages.
(PCT/US2015/062137) Invitation to Pay Additional Fees and, where applicable, protest fee.
U.S. Appl. No. 14/174,514, filed Feb. 6, 2014.
(PCT/US2015/013729) PCT Notification of Transmittal of the International Search Report and the Written Opinion of the International Searching Authority.
(PCT/US2014/070598) PCT Notification of Transmittal of the International Search Report and the Written Opinion of the International Searching Authority.
U.S. Appl. No. 14/552,758, filed Nov. 25, 2014.
(PCT/US2015/027055) PCT Notification of Transmittal of the International Search Report and the Written Opinion of the International Searching Authority, dated Sep. 30, 2015, 9 pages.
Telectronics Meta 1254 DDDr Physician Manual, Chapter 8 (46 pages).
Telectronics Meta 1254 DDDr Physician Manual (55 pages).
(PCT/US2016/049573) PCT Notification of Transmittal of the International Search Report and the Written Opinion of the International Searching Authority, dated Nov. 28, 2016, 10 pages.

* cited by examiner

RATE RESPONSIVE CARDIAC PACING CONTROL USING POSTURE

TECHNICAL FIELD

The disclosure relates to pacemakers capable of monitoring patient activity and patient body posture and an associated method for controlling rate responsive pacing based on activity and body posture.

BACKGROUND

A variety of implantable medical devices (IMDs) for delivering a therapy, monitoring a physiological condition of a patient or a combination thereof have been clinically implanted or proposed for clinical implantation in patients. Some IMDs may employ one or more elongated electrical leads carrying stimulation electrodes, sense electrodes, and/or other sensors. Other IMDs may incorporate electrodes and/or other sensors along or within a housing of the IMD that encloses circuitry and electronic components of the IMD.

IMDs may deliver therapy to and/or monitor conditions of a variety of organs, nerves, muscle or tissue, such as the heart, brain, stomach, spinal cord, pelvic floor, or the like. Some IMDs, such as cardiac pacemakers, monitor a patient's heart activity and provide therapeutic electrical stimulation to the heart of the patient via electrodes coupled to the pacemaker. The electrical stimulation provided by the IMD may include signals such as pacing pulses to address abnormal cardiac rhythms such as bradycardia.

In some cases, the IMD senses a signal representative of the metabolic demand of the patient in order to provide cardiac pacing at a rate intended to meet the metabolic demand of the patient. For example, an indication of the patient's physical activity level may be determined from an accelerometer signal correlated to physical activity in order provide rate responsive pacing to dynamically maintain a heart rate that meets the metabolic demand of the patient.

SUMMARY

In general, the disclosure is directed to techniques for cardiac rate responsive pacing based on patient activity and patient body posture. A pacemaker operating in accordance with the techniques disclosed herein determines an activity metric from an activity sensor signal and derives a sensor-indicated pacing rate from the activity metric. If the sensor indicated pacing rate indicates that an increase in pacing rate is needed, the pacemaker verifies that the patient body posture corresponds to an exercising posture before adjusting the pacing rate to the sensor-indicated pacing rate. If an established exercising body posture is not verified, the pacemaker withholds the rate response adjustment to the sensor indicated pacing rate and sets a pacing rate that is not correlated to the activity metric.

In one example, the disclosure provides a method including sensing an activity signal correlated to a metabolic demand of a patient, sensing a posture signal correlated to a physical body posture of the patient, determining a sensor indicated pacing rate from the activity signal, comparing the posture signal to a verification criteria for confirming an exercising posture of the patient, and withholding an adjustment to the sensor indicated pacing rate responsive to the verification criteria not being met.

In another example, the disclosure provides an implantable rate responsive pacemaker including a sensor module, a pulse generator, and a control module. The sensor module is configured to produce an activity signal correlated to a metabolic demand of a patient and a posture signal correlated to patient posture. The pulse generator is configured to generate and deliver pacing pulses to a patient's heart via a pair of electrodes coupled to the pacemaker. The control module is coupled to the pulse generator and the sensor module and is configured to determine a sensor indicated pacing rate from the activity signal, compare the posture signal to verification criteria for confirming an exercising posture of the patient, and withhold an adjustment of a pacing rate to the sensor indicated pacing rate responsive to the verification criteria not being met.

In another example, the disclosure provides a non-transitory, computer readable storage medium storing a set of instructions that, when executed by a control module of an implantable pacemaker, cause the pacemaker to determine a sensor indicated pacing rate from an activity signal correlated to a metabolic demand of a patient and received by the control module from a sensor module, compare a posture signal received by the control module from the sensor module and correlated to patient body posture to verification criteria, and withhold an adjustment of a pacing rate to the sensor indicated pacing rate responsive to the verification criteria not being met.

This summary is intended to provide an overview of the subject matter described in this disclosure. It is not intended to provide an exclusive or exhaustive explanation of the apparatus and methods described in detail within the accompanying drawings and description below. Further details of one or more examples are set forth in the accompanying drawings and the description below.

DETAILED DESCRIPTION

An implantable medical device (IMD) system is described herein that includes a pacemaker having a sensor for producing a signal correlated to patient activity and patient posture. The sensor signal is used for determining a sensor-indicated pacing rate, referred to as a "sensor-indicated rate" or "SIR," to provide rate-responsive cardiac pacing that is automatically adjusted to meet the patient's metabolic demand based on detected patient activity. The sensor, which may be a motion-based sensor such as an accelerometer that is subjected to patient body motion during activity or exercise, may be subjected to heart motion. As used in this disclosure, the adverb "when" in the context of the IMD operation is used to refer to a triggering condition that initiates or triggers a desired response by the IMD.

Heart motion may contribute to an accelerometer sensor signal to a greater or lesser degree depending at least in part on the body posture of the patient and the position of the pacemaker relative to the heart. In some examples, the pacemaker may be an intracardiac pacemaker such that the accelerometer included in the pacemaker is implanted within a heart chamber. When the patient is lying down, particularly in a side-lying position, the accelerometer may be subjected to cardiac motion to a greater degree than when the patient is in an upright position due to the position of the intracardiac pacemaker (and accelerometer) within the heart. The cardiac motion contributing to the motion-based activity sensor signal may cause an artificially high, SIR to be determined and applied to the patient when the patient is actually at rest. Techniques disclosed herein enable the pacemaker to control the pacing rate response to a SIR based on patient posture. The patient posture may override a decision to increase the pacing rate, even when a metric of patient activity derived from the sensor signal indicates a high level of activity above a resting level. For example, if the SIR is greater than a normal, resting pacing rate when the posture signal is correlated to a posture that is not established as an exercising or active posture of the patient, the pacing rate response to the SIR may be withheld such that the pacing rate applied to the patient is not correlated to the SIR responsive to an exercising posture not being detected.

Figure 1:
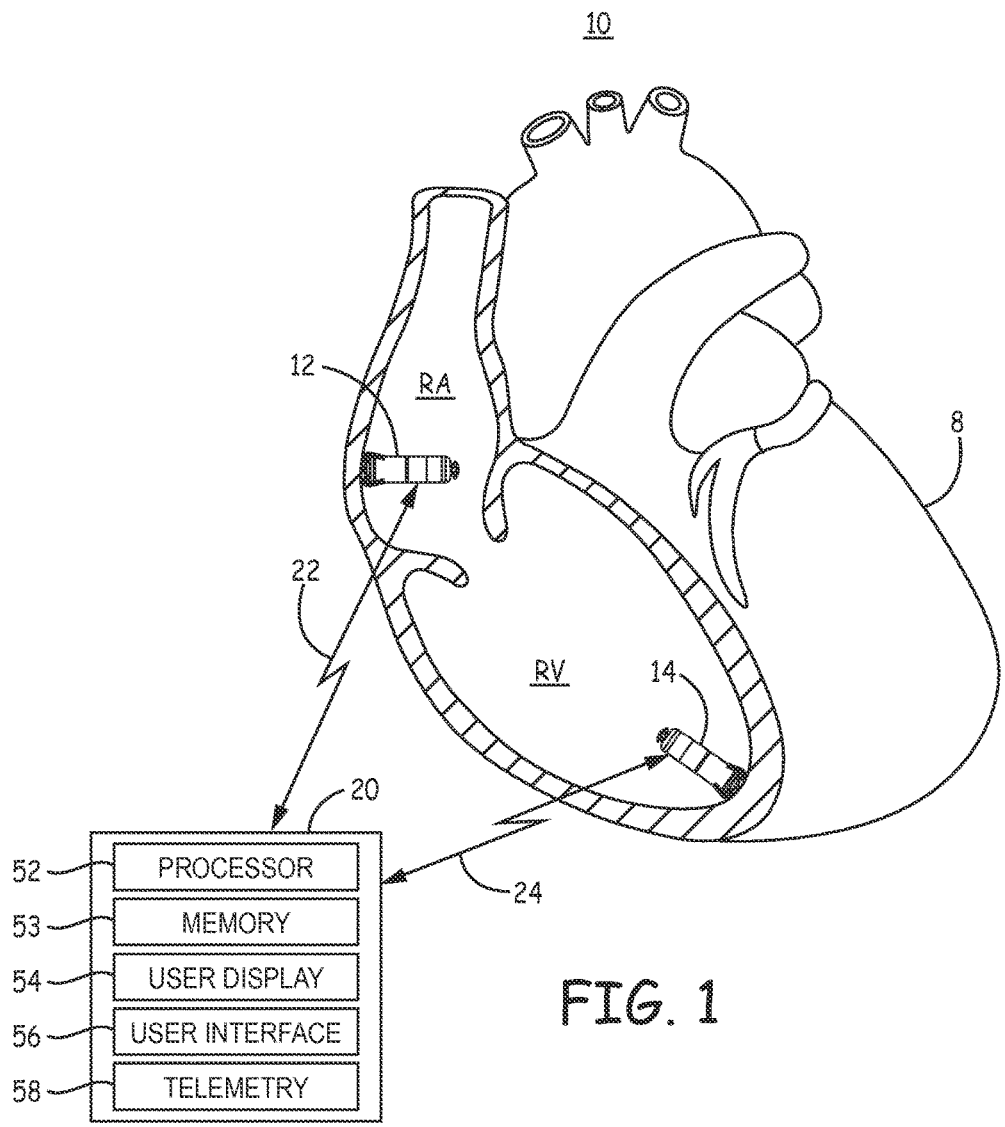
FIG. 1 is a conceptual diagram illustrating an intracardiac pacing system that may be used to sense cardiac electrical signals and provide therapy to a patient's heart.

FIG. 1 is a conceptual diagram illustrating an intracardiac pacing system 10 that may be used to sense cardiac electrical signals and provide therapy to a patient's heart 8. IMD system 10 includes a right ventricular (RV) intracardiac pacemaker 14 and a right atrial (RA) intracardiac pacemaker 12. A cardiac pacing system employing the techniques disclosed herein is not limited to a system including both a RA pacemaker 12 and a RV pacemaker 14 as shown. Both pacemakers 12 and 14 are shown to illustrate example implant locations of a pacemaker that may implement the disclosed techniques. A cardiac pacing system employing the disclosed techniques, however, may include one or more pacemakers, such as pacemaker 12 or 14, configured to be positioned inside or outside heart 8. A pacemaker performing the methods described in conjunction with the flow charts presented herein may include a motion-based patient activity sensor that is subjected to the motion of the beating heart 8 in at least some or all patient postures.

In the example shown, pacemakers 12 and 14 are transcatheter intracardiac pacemakers adapted for implantation within the heart, e.g., within the RV, within the left ventricle (LV), within the RA or within the left atrium (LA) of heart 8. RA pacemaker 12 is shown positioned along an endocardial wall of the RA, e.g., along the RA lateral wall or RA septum. RV pacemaker 14 is shown positioned along an endocardial wall of the RV, e.g., near the RV apex. The techniques disclosed herein, however, are not limited to the pacemaker locations shown in the example of FIG. 1 and other relative locations within or along the respective heart chambers are possible.

Pacemakers 12 and 14 are reduced in size compared to subcutaneously implanted pacemakers and are generally cylindrical in shape to enable transvenous implantation via a delivery catheter. In other examples, pacemakers 12 and 14 may be implanted outside heart 8, including epicardial locations. For example, pacemaker 12 may be positioned outside or within the right atrium or left atrium to provide respective right atrial or left atrial pacing. Pacemaker 14 may be positioned outside or within the right ventricle or left ventricle to provide respective right ventricular or left ventricular pacing.

Pacemakers 12 and 14 are each capable of producing electrical stimulation pulses, e.g., pacing pulses, delivered to heart 8 via one or more electrodes on the outer housing of the pacemaker. RA pacemaker 12 is configured to sense an intracardiac electrogram (EGM) signal in the RA using the housing based electrodes and deliver RA pacing pulses. RV pacemaker 14 is configured to sense an EGM signal in the RV using housing based electrodes and deliver RV pacing pulses.

At least one of pacemakers 12 or 14 is equipped with an activity sensor that produces a signal responsive to patient motion, e.g., a three dimensional accelerometer. The pacemaker determines an activity metric from the activity sensor signal and derives a SIR based on the activity metric. The pacemaker may be configured to determine a posture signal from at least one of the activity sensor axes or a combination of axes. In other examples, a posture sensor may be provided separately from the activity sensor. If the posture signal meets criteria for confirming a posture that is likely to be an exercising posture for the patient, the pacemaker adjusts the pacing rate to the SIR. If the patient posture is not confirmed to be an exercising posture, the adjustment to the SIR may be withheld, resulting in a pacing rate that is not correlated to the SIR.

Pacemakers 12 and 14 are each capable of bidirectional wireless communication with an external device 20. External device 20 is often referred to as a "programmer" because it is typically used by a physician, technician, nurse, clinician or other qualified user for programming operating parameters in pacemakers 12 and 14 as well as for retrieving device- and/or patient-related data from pacemakers 12 and 14. External device 20 may be located in a clinic, hospital or other medical facility. External device 20 may alternatively be embodied as a home monitor or a handheld device that may be used in a medical facility, in the patient's home, or another location. Operating parameters, such as sensing and therapy delivery control parameters, may be programmed into pacemakers 12 and 14 using external device 20. Aspects of external device 20 may generally correspond to the external programming/monitoring unit disclosed in U.S. Pat. No. 5,507,782 (Kieval, et al.), incorporated herein by reference in its entirety.

External device 20 includes a processor 52, memory 53, user display 54, user interface 56 and telemetry module 58. Processor 52 controls external device operations and processes data and signals received from pacemakers 12 and 14. According to techniques disclosed herein, processor 52 may be used to transmit signals to RA pacemaker 12 and/or RV pacemaker 14 when the patient is in a known body posture to enable the respective pacemaker to establish a posture signal representative of the known body posture. The known body posture may be an expected exercising posture, such as an upright posture, during which an SIR is used to control the rate responsive pacing rate. In other examples, a known posture signal may be established for an unexpected exercising posture, such as a non-upright posture, e.g., a side-lying posture, during which an increase to a SIR that is greater than a programmed lower rate may be withheld.

In various examples, external device 20 may be used to transmit signals to pacemaker 12 and/or pacemaker 14 to indicate when a known patient body posture is assumed, when the patient is at rest, when the patient is active, and/or when the patient is anticipating exercise onset. As described below, pacemaker 12 and/or pacemaker 14 may respond to these transmitted signals for establishing an activity signal axis and/or a posture signal axis for monitoring patient activity and posture, respectively, using a multi-axis accelerometer.

Processor 52 may provide user display 54 with data for generating a graphical user interface to a user for selecting and programming control parameters used in controlling rate responsive pacing by pacemaker 12 or pacemaker 14 as well as other pacemaker functions. External device 20 may display other data and information relating to pacemaker 12 or 14 functions to a user for reviewing pacemaker operation and programmed parameters as well as EGM signals or other physiological data that are retrieved from pacemakers 12 and 14 during an interrogation session. User interface 56 may include a mouse, touch screen, keyboard and/or keypad to enable a user to interact with external device 20 to initiate a telemetry session with pacemakers 12 and 14 for retrieving data from and/or transmitting data to pacemakers 12 and 14 for selecting and programming desired sensing and therapy delivery control parameters.

Telemetry module 58 is configured for bidirectional communication with an implantable telemetry module included in pacemakers 12 and 14. Telemetry module 58 establishes a wireless radio frequency (RF) communication link 22 with RA pacemaker 12 and wireless RF communication link 24 with RV pacemaker 14 using a communication protocol that appropriately addresses the targeted pacemaker 12 or 14. An example RF telemetry communication system that may be implemented in system 10 is generally disclosed in U.S. Pat. No. 5,683,432 (Goedeke, et al.), hereby incorporated herein by reference in its entirety. Telemetry module 58 is configured to operate in conjunction with processor 52 for sending and receiving data relating to pacemaker functions via communication link 22 or 24. Communication links 22 and 24 may be established between respective RA pacemaker 12 and RV pacemaker 14 and external device 20 using a radio frequency (RF) link in the Medical Implant Communication Service (MICS) band, Medical Data Service (MEDS) band, BLUETOOTH® or Wi-Fi or other communication bandwidth.

Telemetry module 58 may be capable of bi-directional communication with pacemakers 12 and 14 over a wide range of distances, e.g., up to approximately 10 meters. In other examples, telemetry communication may require the use of a programming head placed in proximity of RA pacemaker 12 or RV pacemaker 14 to facilitate data transfer. It is contemplated that external device 20 may be in wired or wireless connection to a communications network via telemetry module 58 for transferring data to a remote database or computer to allow remote management of the patient 12.

Figure 2A:
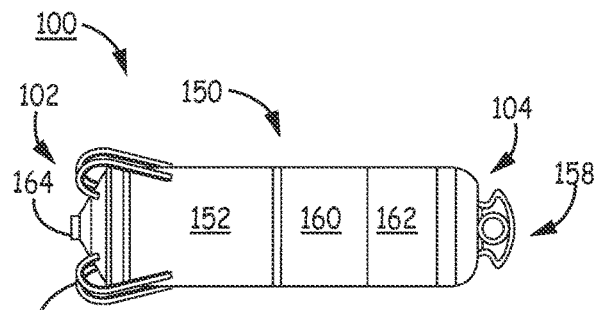
FIG. 2A is a conceptual diagram of an intracardiac pacemaker that may correspond to the right atrial pacemaker or the right ventricular pacemaker shown in FIG. 1.

FIG. 2A is a conceptual diagram of an intracardiac pacemaker 100 that may correspond to RA pacemaker 12 or RV pacemaker 14 shown in FIG. 1. Pacemaker 100 includes electrodes 162 and 164 spaced apart along the housing 150 of pacemaker 100 for sensing cardiac EGM signals and delivering pacing pulses. Electrode 164 is shown as a tip electrode extending from a distal end 102 of pacemaker 100, and electrode 162 is shown as a ring electrode along a mid-portion of housing 150, for example adjacent proximal end 104. Distal end 102 is referred to as "distal" in that it is expected to be the leading end as it advanced to an implant site using a delivery tool, such as a catheter, and placed against a target pacing site.

Electrodes 162 and 164 form an anode and cathode pair for bipolar cardiac pacing and sensing. Electrodes 162 and 164 may be positioned on or as near as possible to respective proximal and distal ends 104 and 102 to increase the inter-electrode spacing between electrodes 162 and 164. In alternative embodiments, pacemaker 100 may include two or more ring electrodes, two tip electrodes, and/or other types of electrodes exposed along pacemaker housing 150 for delivering electrical stimulation to heart 8 and sensing EGM signals. Electrodes 162 and 164 may be, without limitation, titanium, platinum, iridium or alloys thereof and may include a low polarizing coating, such as titanium nitride, iridium oxide, ruthenium oxide, platinum black among others.

Housing 150 is formed from a biocompatible material, such as a stainless steel or titanium alloy. In some examples, the housing 150 may include an insulating coating. Examples of insulating coatings include parylene, urethane, PEEK, or polyimide among others. The entirety of the housing 150 may be insulated, but only electrodes 162 and 164 uninsulated. In other examples, the entirety of the housing 150, isolated from tip electrode 164, may function as an electrode instead of providing a localized electrode, such as electrode 162, to serve as a return anode electrode.

The housing 150 includes a control electronics subassembly 152, which houses the electronics for sensing cardiac signals, producing pacing pulses and controlling therapy delivery and other functions of pacemaker 100. Housing 150 further includes a battery subassembly 160, which provides power to the control electronics subassembly 152. Battery subassembly 160 may include features of the batteries disclosed in commonly-assigned U.S. Pat. No. 8,433,409 (Johnson, et al.) and U.S. Pat. No. 8,541,131 (Lund, et al.), both of which are hereby incorporated by reference herein in their entirety.

Pacemaker 100 may include a set of fixation tines 166 to secure pacemaker 100 to patient tissue, e.g., by interacting with the ventricular trabeculae or actively engaging endocardial tissue. Fixation tines 166 are configured to anchor pacemaker 100 to position electrode 164 in operative proximity to a targeted tissue for delivering therapeutic electrical stimulation pulses. Numerous types of active and/or passive fixation members may be employed for anchoring or stabilizing pacemaker 100 in an implant position. Pacemaker 100 may include a set of fixation tines as disclosed in commonly-assigned, pre-grant publication U.S. 2012/0172892 (Grubac, et al.), pending, hereby incorporated herein by reference in its entirety.

Pacemaker 100 may further include a delivery tool interface 158. Delivery tool interface 158 may be located at the proximal end 104 of pacemaker 100 and is configured to connect to a delivery device, such as a catheter, used to position pacemaker 100 at an implant location during an implantation procedure, for example within a heart chamber.

Figure 2B:
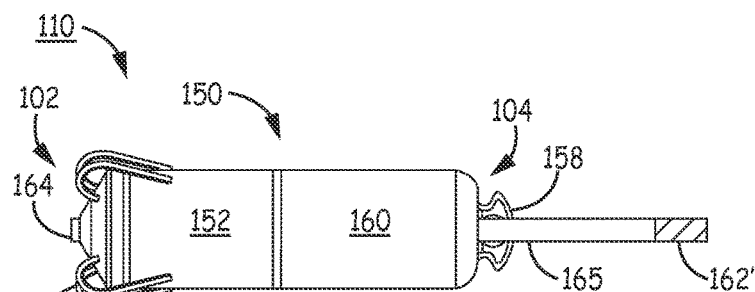
FIG. 2B is a conceptual diagram of an alternative embodiment of an intracardiac pacemaker.

FIG. 2B is a conceptual diagram of an alternative embodiment of an intracardiac pacemaker 110. Pacemaker 110 includes housing 150, control assembly 152, battery assembly 160, fixation member 166 and electrode 164 along a distal end 102, and may include a delivery tool interface 158 along the proximal end 104 as described above in conjunction with FIG. 2A. Pacemaker 110 is shown to include a return sensing electrode 162' extending away from housing 150 along a proximal sensing extension 165. As such, instead of carrying a pair of electrodes along the housing 150, which limits the maximum possible inter-electrode spacing, a proximal sensing extension 165 may be coupled to the housing 150 for positioning a return sensing electrode 162', which may be electrically coupled to housing 150, at an increased inter-electrode distance from distal tip electrode 164.

Figure 2C:
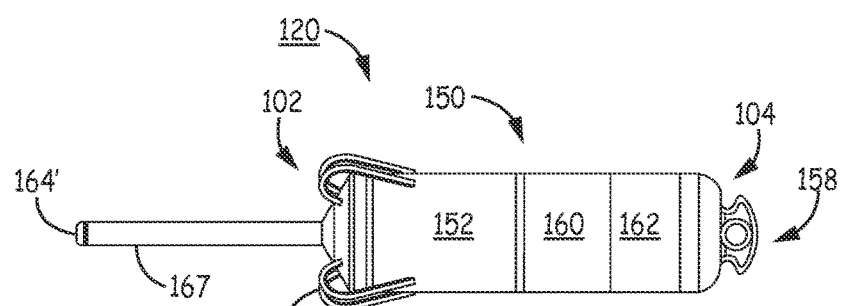
FIG. 2C is a conceptual diagram of yet another embodiment of an intracardiac pacemaker.

FIG. 2C is a conceptual diagram of an alternative embodiment of intracardiac pacemaker 120 having a distal extension 167 coupled to the distal end 102 of pacemaker housing 150 to extend distal electrode 164' away from electrode 162 positioned along housing 150 near or at proximal end 104. Distal extension 167 is an insulated electrical conductor that may electrically couple electrode 164' to pacemaker circuitry within control electronics assembly 152 via an electrical feedthrough crossing housing 150. Pacemaker 120 having an insulated, electrically conductive extender 167 for increasing the inter-electrode spacing may correspond generally to the implantable device and flexible conductor disclosed in commonly-assigned U.S. Pat. No. 8,758,365 (Bonner, et al.), incorporated herein by reference in its entirety.

In the examples shown in FIGS. 2A, 2B and 2C, an activity sensor for producing a signal correlated to patient activity may be enclosed in control electronics assembly 152. In other examples, an activity sensor may be located along any other portion of housing 150 or along an extension 165 or 167. The activity sensor may be embodied as a piezoelectric accelerometer in some examples.

Figure 3:
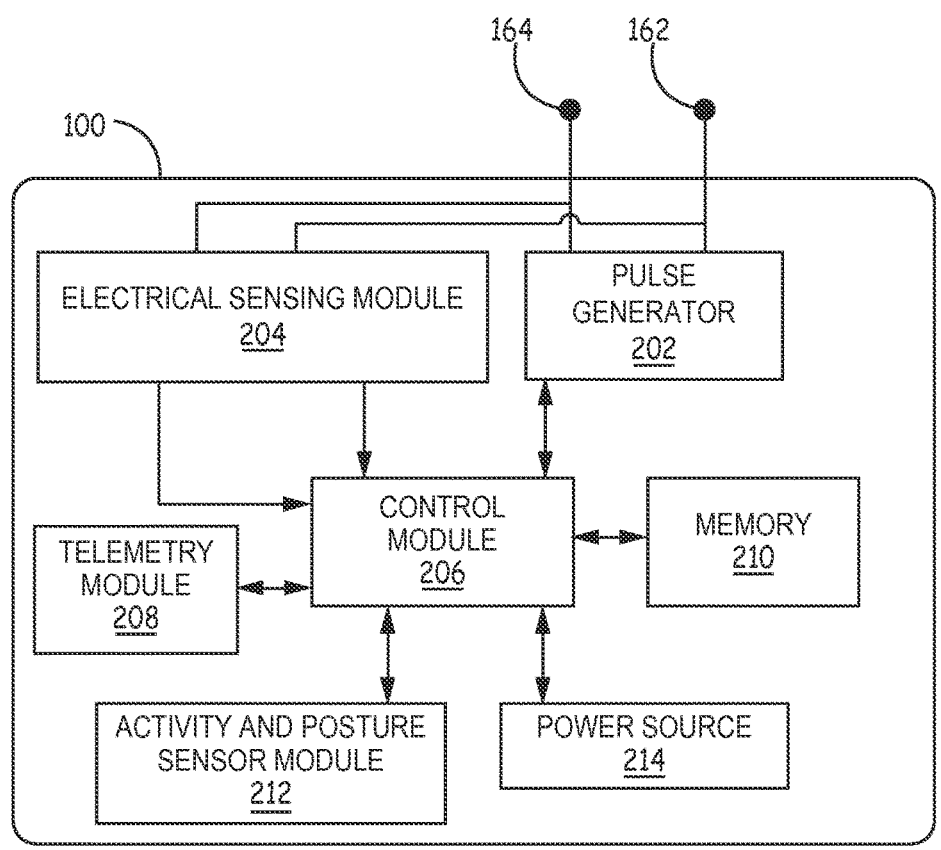
FIG. 3 is a functional block diagram of an example configuration of the intracardiac pacemaker shown in FIG. 2A.

FIG. 3 is a functional block diagram of an example configuration of pacemaker 100 shown in FIG. 2A. Pacemaker 100 includes a pulse generator 202, an electrical sensing module 204, a control module 206, memory 210, telemetry module 208, an activity and posture sensor module 212, and a power source 214. As used herein, the term "module" refers to an application specific integrated circuit (ASIC), an electronic circuit, a processor (shared, dedicated, or group) and memory that execute one or more software or firmware programs, a combinational logic circuit, a microelectromechanical system (MEMs), or other suitable components that provide the described functionality. Each of RA pacemaker 12 and RV pacemaker 14 may include similar modules as represented by the pacemaker 100 shown in FIG. 3; however it is understood that the modules are configured differently as needed to perform the functionality of the separate RA and RV pacemakers 12 and 14.

For example, responsive to pacemaker 100 being configured to operate as RV pacemaker 14, control module 206 is configured to set various ventricular pacing escape intervals used to control delivery of ventricular pacing pulses. When pacemaker 100 is embodied as RA pacemaker 12, control module 206 is configured to set atrial pacing escape intervals to control delivery of RA pacing pulses.

The functions attributed to pacemaker 100 herein may be embodied as one or more processors, controllers, hardware, firmware, software, or any combination thereof. Depiction of different features as specific circuitry or modules is intended to highlight different functional aspects and does not necessarily imply that such functions must be realized by separate hardware or software components or by any particular architecture. Rather, functionality associated with one or more modules, processors, or circuits may be performed by separate hardware or software components, or integrated within common hardware or software components. For example, pacing control operations performed by pacemaker 100 may be implemented in control module 206 executing instructions stored in associated memory 210 and relying on input from electrical sensing module 204 and activity and posture sensor module 212.

Pulse generator 202 generates electrical stimulation pulses that are delivered to heart tissue via electrodes 162 and 164 under the control of control module 206. Electrodes 162 and 164 may be housing-based electrodes as shown in FIG. 2A, but one or both electrodes 162 and 164 may alternatively be carried by an insulated, electrical conductor extending away from the pacemaker housing as described in conjunction with FIGS. 2B and 2C.

Pulse generator 202 may include one or more capacitors and a charging circuit to charge the capacitor(s) to a programmed pacing pulse voltage. At appropriate times, as controlled by a pace timing and control module included in control module 206, the capacitor is coupled to pacing electrodes 162 and 164 to discharge the capacitor voltage and thereby deliver the pacing pulse. Pacing circuitry generally disclosed in the above-incorporated U.S. Pat. No. 5,507,782 (Kieval, et al.) and in commonly assigned U.S. Pat. No. 8,532,785 (Crutchfield, et al.), incorporated herein by reference in its entirety, may be implemented in pacemaker 100 for charging a pacing capacitor to a predetermined pacing pulse amplitude under the control of control module 206 and delivering a pacing pulse.

Control module 206 controls pulse generator 202 to deliver a pacing pulse in response to expiration of a pacing escape interval according to programmed therapy control parameters stored in memory 210. The pace timing and control module included in control module 206 may include an escape interval timer or counter that is set to a pacing escape interval used for controlling the timing of pacing pulses relative to a paced or sensed event. Upon expiration of a pacing escape interval, a pacing pulse is delivered. If a cardiac event is sensed during the pacing timing interval by electrical sensing module 204, the scheduled pacing pulse may be inhibited, and the pacing escape interval may be reset to a new time interval.

As described below, control module 206 uses a signal from activity and posture sensor module 212 for determining an SIR used to control the rate of pacing pulse delivery. For example, an escape interval timer included in control module 206 may be set to a pacing escape interval corresponding to an SIR, and the pacing escape interval may be adjusted as the SIR changes in response to an activity sensor signal, as long as a posture signal received from activity and posture sensor module 212 meets criteria for confirming an exercising posture (or at least does not indicate a non-exercising posture).

Electrical sensing module 204 receives cardiac EGM signals developed across electrodes 162 and 164. A cardiac event may be sensed by electrical sensing module 204 responsive to the EGM signal crossing a sensing threshold, which may be an auto-adjusting sensing threshold. In response to a sensing threshold crossing, electrical sensing module 204 passes a sensed event signal to control module 206 for use in controlling the timing of pacing pulses. For example, upon receipt of a sensed event signal, control module 206 may start a pacing escape interval set according to the currently established pacing rate, based on the SIR and patient posture. If another sensed event signal is received before the pacing escape interval expires, the escape interval may be restarted and the scheduled pacing pulse is inhibited. If the pacing escape interval expires without receiving a sensed event signal, the pulse generator 202 delivers a pacing pulse. Control module 206 may adjust the pacing escape interval based on the activity-based SIR and a posture signal as described in greater detail below.

Memory 210 may include computer-readable instructions that, when executed by control module 206, cause control module 206 to perform various functions attributed throughout this disclosure to pacemaker 100. The computer-readable instructions may be encoded within memory 210. Memory 210 may include any non-transitory, computer-readable storage media including any volatile, non-volatile, magnetic, optical, or electrical media, such as a random access memory (RAM), read-only memory (ROM), non-volatile RAM (NVRAM), electrically-erasable programmable ROM (EEPROM), flash memory, or other digital media with the sole exception being a transitory propagating signal. Memory 210 stores timing intervals, counters, or other data used by control module 206 to control the delivery of pacing pulses by pulse generator 202. For example, memory 210 may store set points and slope relationships used in determining the SIR based on a signal from activity and posture sensor module 212 received by control module 206. Criteria for controlling rate responsive pacing based on patient posture may also be stored in memory 210 and accessed by control module 206 as needed for making decisions on pacing escape interval adjustments.

Activity and posture sensor module 212 may be embodied as a piezoelectric or MEMs accelerometer for producing a signal correlated to patient body motion. The use of an accelerometer in an intracardiac device for obtaining a patient activity signal is generally disclosed in pending U.S. Pat. Publication No. 2015/0217119 (Nikolski, et al.), incorporated herein by reference in its entirety. The use of a patient activity signal for providing rate-responsive pacing is generally disclosed in U.S. Pat. No. 7,031,772 (Condie, et al.), incorporated herein by reference in its entirety. A multi-dimensional accelerometer for detecting patient posture changes is generally disclosed in in U.S. Pat. No. 5,593,431 (Sheldon), hereby incorporated herein by reference in its entirety. In some examples, one dimension of a multi-axis accelerometer may be used for detecting patient posture and the same or another dimension of the multi-axis accelerometer may be used for detecting patient activity. As such, activity and posture sensor module 212 may include a multi-axis accelerometer that provides signals from one or more axes to control module 206 for use in determining patient activity metrics and for monitoring patient posture. Control module 206 may select which axis signals are used for determining patient activity metrics and for determining patient posture.

In other examples, activity and posture sensor module 212 may include separate sensors for detecting patient activity and patient posture. For example a one-dimensional or multi-dimensional accelerometer may be used for detecting patient posture. A second one-dimensional or multi-dimensional accelerometer may be used for detecting patient activity. Generally, any motion-based sensor producing a signal correlated to movement of the patient's body may be used for monitoring patient activity.

Control module 206 receives an activity signal from activity and posture sensor module 212 and determines an activity metric from the signal at predetermined time intervals or activity sampling rates for use in determining the SIR. The SIR may vary between a programmed lower rate (LR) during periods of rest and a programmed maximum upper pacing rate during periods of maximum exertion. The SIR may be derived from an activity metric according to a SIR transfer function as described below, which may include different rates of change of the SIR over different ranges of the activity metric.

In some examples, the activity metric is determined as an activity count. In these instances, control module 206 includes a counter to track the activity count as the number of times the activity signal from activity and posture sensor module 212 crosses a threshold during an activity count interval, for example a 2-second interval. The count at the end of each activity count interval is correlated to patient body motion during the activity count interval and is therefore expected to be correlated to patient metabolic demand. The threshold applied to the activity sensor signal, which when crossed by the activity sensor signal causes the activity count to be increased, may be a default or programmable threshold or may be an automatically adjusted threshold. Methods for obtaining an activity count over an n-second interval and for adjusting the activity sensor signal threshold used for obtaining the activity count are generally disclosed in commonly-assigned U.S. Pat. No. 5,720,769 (van Oort), incorporated herein by reference in its entirety. In other examples, an activity metric may be obtained from the activity sensor signal by integrating or summing activity signal sample points over an activity count interval, e.g., a two-second interval though longer or shorter intervals of time may be used for determining an activity metric.

Techniques are disclosed herein for controlling the rate response behavior of pacemaker 100 based on patient posture and may be implemented in conjunction with any type of activity sensor that has a tendency to produce a signal that includes cardiac activity and therefore indicates a non-zero patient activity level due to cardiac activity even in the absence of actual physical activity or exertion by the patient. Other types of activity sensors may produce a signal correlated to respiratory activity, such as minute ventilation, blood or tissue oxygen saturation, or another indication of the patient's body motion or physical activity. Various examples of other types of implantable sensors that may be implemented with a rate responsive pacemaker for controlling pacing rate based on metabolic demand are generally described in U.S. Pat. No. 5,755,740 (Nappholz), U.S. Pat. No. 5,507,785 (Deno), and U.S. Pat. No. 5,312,454 (Roline). The techniques disclosed herein may be utilized in any pacemaker system having an activity sensor that produces a signal from which an activity metric is derived that is both activity and posture dependent where the posture dependency results in falsely high activity metrics to be determined during periods of inactivity.

Power source 214 provides power to each of the other modules and components of pacemaker 100 as required. Control module 206 may execute power control operations to control when various components or modules are powered to perform various pacemaker functions. Power source 214 may include one or more energy storage devices, such as one or more rechargeable or non-rechargeable batteries. The connections between power source 214 and other pacemaker modules and components are not shown in FIG. 3 for the sake of clarity.

Telemetry module 208 includes a transceiver and associated antenna for transferring and receiving data from external device 20 via a radio frequency (RF) communication link as described above. Pacemaker 100 may receive pacing and sensing control parameter values that are stored in memory 210 and accessed by control module 206 via programming commands received by telemetry module 208 from external device 20. Telemetry module 208 may also be used for communication with another IMD implanted in the patient, e.g., communication between pacemaker 12 and pacemaker 14 in FIG. 1.

Figure 4:
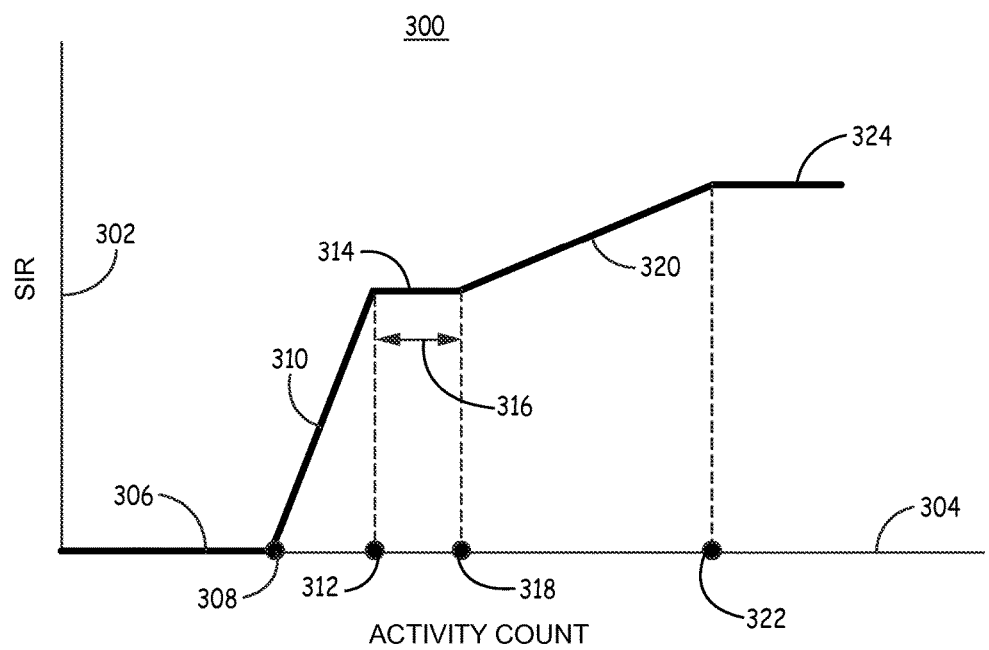
FIG. 4 is a plot of a sensor-indicated rate (SIR) transfer function determined by the pacemaker of FIG. 3 using activity counts determined from an accelerometer signal according to one example.

FIG. 4 is an example plot 300 of a SIR transfer function that may be used by pacemaker 100 according to one illustrative example. In plot 300, SIR is plotted along the y-axis 302 as a function of activity count plotted along the x-axis 304. Control module 206 may establish a lower rate (LR) set point 308 that may be programmed by a user or set by control module 206 based on an analysis of the activity counts determined over an interval of time such as one or more days or one or more weeks. The pacing rate is not adjusted above a lower rate 306, also referred to herein as the "base pacing rate," as long as the activity count is at or below the LR set point 308.

As the activity count increases above the LR set point 308, the SIR may be determined according to an established profile between the SIR and the activity count. For example, an activities of daily living (ADL) lower set point 312 and ADL upper set point 318 may be established as the lower and upper boundaries of an activity count range that is expected to encompass the patient's activity level during normal daily activities and light to moderate activity, such as moving about the house, driving a car, light chores, etc. The SIR may be increased from the LR 306 to the ADL rate 314 according to a slope 310 between the LR set point 308 and the ADL lower set point 312. The SIR remains at the ADL rate 314 over the ADL range 316 between activity counts ranging from the ADL lower set point 312 and the ADL upper set point 318.

If the activity count is above the upper ADL set point 318, the SIR is adjusted according to a second slope 320 as a function of activity count up to a maximum upper rate set point 322. The SIR is a maximum upper pacing rate 324 for all activity counts greater than the maximum upper rate set point 322. Each of the lower ADL set point 312, upper ADL set point 318 and maximum upper rate set point 322 may be tailored to a patient's particular needs based on activity count history and/or known exercise and ADL patterns.

The SIR transfer function shown in FIG. 4 is one example of a transfer function used to convert an activity metric determined from an activity sensor to the SIR. Practice of the techniques disclosed herein is not limited to a particular transfer function or method of determining the SIR from an activity sensor signal.

Figure 5:
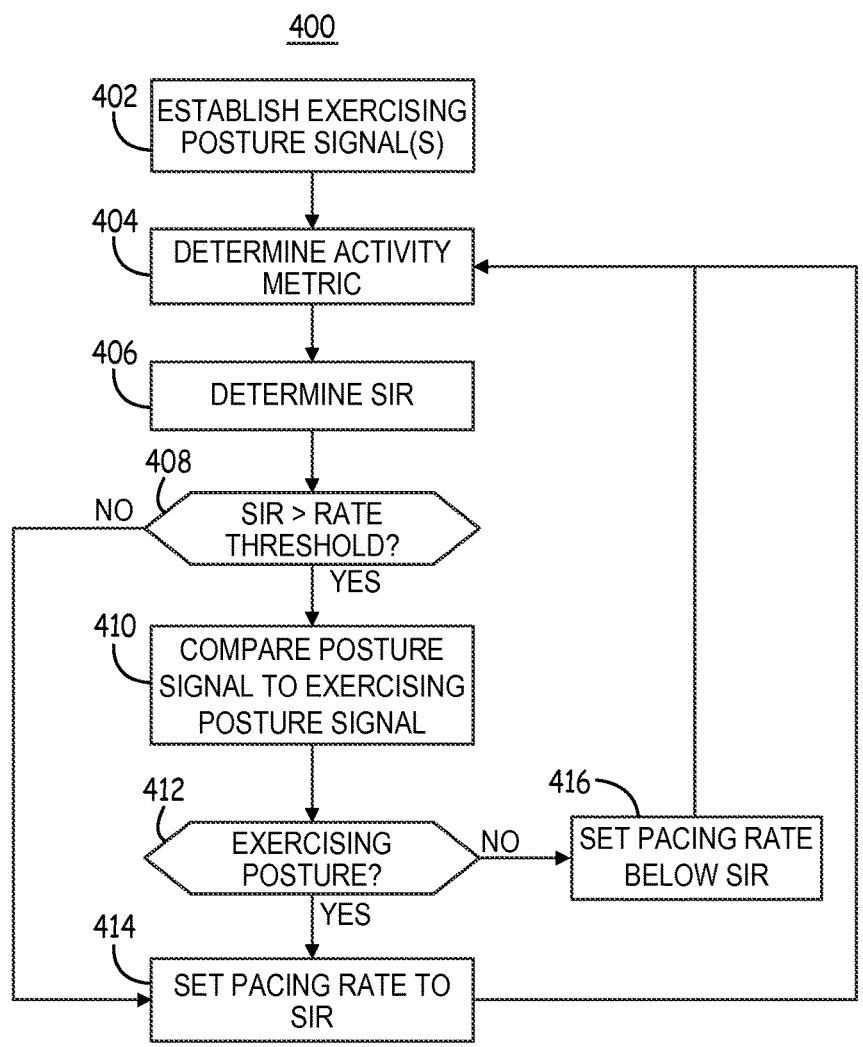
FIG. 5 is a flow chart of a method performed by a pacemaker for controlling rate responsive pacing based on patient posture according to one example.

FIG. 5 is a flow chart 400 of a method performed by pacemaker 100 for controlling rate responsive pacing based on patient posture according to one example. Flow chart 400 and other flow charts presented herein are intended to illustrate the functional operation of the device, and should not be construed as reflective of a specific form of software or hardware necessary to practice the methods described. It is believed that the particular form of software, firmware, hardware or combination thereof will be determined primarily by the particular system architecture employed in the device and by the particular signal sensing and therapy delivery methodologies employed by the device. Providing software, firmware, and/or hardware to accomplish the described functionality in the context of any modern medical device, given the disclosure herein, is within the abilities of one of skill in the art.

Methods described in conjunction with flow charts presented herein may be implemented in a non-transitory computer-readable storage medium that stores instructions for causing a programmable processor to carry out the methods described. A computer-readable storage medium includes but is not limited to any volatile or non-volatile media, such as a RAM, ROM, CD-ROM, NVRAM, EEPROM, flash memory, and the like with the sole exception being a transitory, propagating signal. The instructions may be implemented as one or more software modules, which may be executed by themselves or in combination with other software.

At block 402, at least one posture signal representative of an expected patient body posture during exercise or activity is established. The posture signal representative of an expected patient body posture during exercise may be established using a single axis or multiple axes of the multi-axis accelerometer. An exercising posture signal established at block 402 will typically include at least an upright posture signal since physical exertion and exercise would typically be performed in an upright position, e.g., walking, jogging, or running or during manual labor. In other examples, however, exercising posture signals established at block 402 may include a posture signal correlated to a prone or semi-prone (e.g., crouched forward) position that may be assumed during swimming or cycling. The exercising posture signal established at block 402 may be tailored to a patient's known exercising habits.

At block 404, control module 206 determines an activity metric from an activity sensor signal received from activity and posture sensor module 202. As indicated above, an activity metric may be determined at regular time intervals, e.g., at two-second intervals. The SIR is determined from the activity metric at block 406, e.g., using an SIR transfer function, such as the one illustrated in FIG. 4. The SIR may be updated after each activity metric is determined or after longer intervals of time according to a rate responsive pacing protocol. The activity sensor signal may be a selected or default axis of a multi-axis accelerometer included in activity and posture sensor module 212.

The SIR is compared to a rate threshold at block 408. The rate threshold may be the lower rate (i.e., base pacing rate). In other examples, the threshold is the ADL rate or may be a selected threshold rate between the lower rate and the ADL rate. If the SIR is not greater than the threshold rate at block 408, the control module 206 sets the pacing rate at the SIR at block 414 without checking the posture signal for verifying an exercising posture. To illustrate, if the threshold rate is the programmed lower rate, and the SIR is not greater than the programmed lower rate, the pacing rate is set to (or maintained at) the lower rate at block 414. In other examples, if the rate threshold is set to the ADL rate, and the SIR is not greater than the ADL rate (block 408), the pacing rate is set to the SIR at block 414, e.g., at or below the ADL rate.

If the SIR is greater than the rate threshold, as determined at block 408, control module 206 compares a posture signal received from activity and posture sensor module 212 to the established exercising posture signal(s) at block 410. If the posture signal is representative of an established exercising posture, as determined at block 412, the control module 206 sets the pacing rate to the SIR. The SIR that is greater than the rate threshold is determined to be a valid SIR correlated to true patient activity when the posture signal represents an established exercising posture. The posture signal may be determined to be representative of an established exercising posture signal when a DC amplitude of a selected posture signal axis (or combination of axes) of a multi-axis accelerometer included in activity and posture sensor module 212 is greater than a posture verification threshold.

If the posture signal does not meet established criteria for verifying an exercising posture signal, the control module 206 sets the pacing rate to a rate that is not correlated to the activity signal metric or the SIR. Pacing at the SIR is withheld when an exercising posture cannot be verified. The elevated SIR may be caused by heart motion contributing to a high activity metric due to patient body posture. The pacing rate set for a non-exercising body posture at block 416 may be below the SIR, e.g., the rate threshold or less than the rate threshold. In some examples, the pacing rate is set to the lower rate at block 416. In other examples, if the rate threshold is the ADL rate, the pacing rate set at block 416 is the ADL rate or a rate between the ADL rate and the lower rate.

Figure 6:
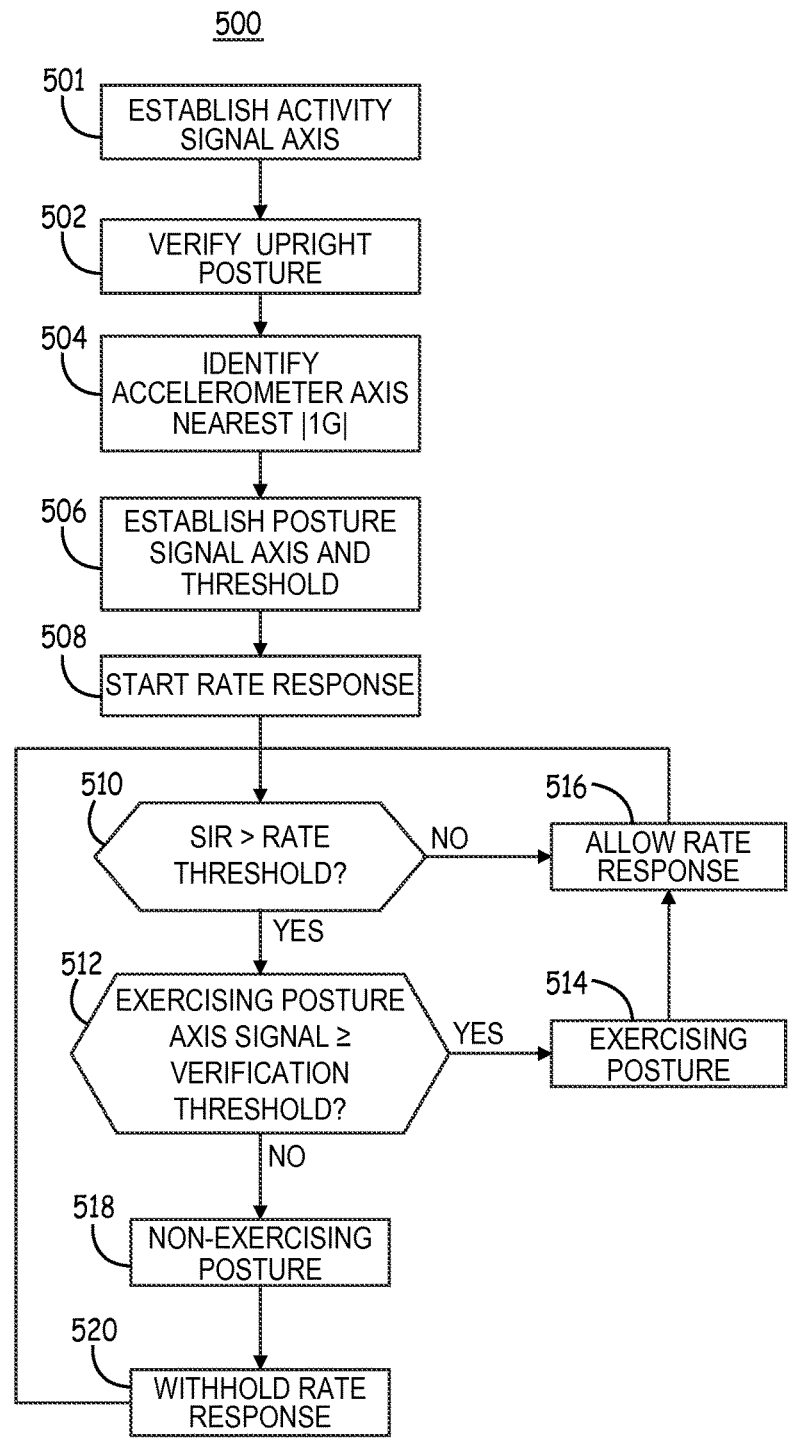
FIG. 6 is a flow chart of a method for controlling rate responsive pacing delivered by a pacemaker according to another example.

FIG. 6 is a flow chart 500 of a method for controlling rate responsive pacing delivered by pacemaker 100 according to another example. At block 501, a patient activity monitoring axis of a multi-axis accelerometer may be established. For example, the patient may be asked to assume multiple postures, e.g., standing, sitting, prone, supine, left-side lying and/or right-side lying, and asked to perform one or more selected exercises, such as walking or stair climbing. External device 20 may be used to transmit a signal to pacemaker 100 to indicate the prescribed posture or activity. One axis of a multi-axis accelerometer, e.g., a three-dimensional accelerometer, may be selected as the activity signal axis based on an analysis of all of the accelerometer axis signals.

For example, for each orthogonal axis of a three-dimensional accelerometer, activity metrics may be determined while the patient assumes one or more resting patient postures and during a prescribed activity. An axis having the least change in activity metrics between different resting patient postures and/or having the greatest change in the activity metrics obtained during the prescribed activity and a resting patient posture may be established as the activity signal axis at block 501. When rate response pacing is enabled, control module 206 determines the SIR from activity metrics determined from the established activity signal axis. It is recognized that in some examples the established activity signal axis may be a virtual axis that is a combination of two or more axes of the multi-dimensional accelerometer.

At block 502, the patient is instructed to assume an upright position, e.g., sitting or standing. The upright position may be verified by a user by transmitting a command from the external device 20 to the pacemaker 100 indicating that the patient posture is an upright posture and that an exercising posture signal should be established by pacemaker 100 for the upright posture.

At block 504, control module 206 identifies an accelerometer axis of a multi-dimensional accelerometer included in activity and posture sensor module 212 that has a DC signal amplitude nearest ±1 G, i.e., an absolute value nearest 1 G. The axis having a signal nearest ±1 G is expected to be an axis most aligned with the force of gravity and therefore represents a vertical axis when the patient is upright. This axis is established as an exercising posture signal axis at block 506 by control module 206. The exercising posture signal axis may be a virtual axis that is a combination of two or more axes of the multi-dimensional accelerometer.

Control module 206 may additionally establish an exercising posture signal threshold at block 506 based on the established exercising posture axis signal received during the verified upright position. For example, if the signal received from the accelerometer axis producing a signal nearest ±1 G is approximately 0.8 G, the exercising posture threshold may be set at ±0.7 G. The exercising posture threshold may be set as a percentage, fixed offset or fixed range relative to the DC signal of the established exercising posture signal axis when the patient posture is verified to be upright. Alternatively, once the exercising posture signal axis is identified, an exercising posture verification threshold may be established at block 506 as a default value, e.g., ±0.6 G, ±0.7 G, ±0.8 G or other predetermined threshold value that is applied to the signal received from the exercising posture signal axis for verifying an exercising posture.

At block 508, if not already enabled, rate responsive pacing is enabled by control module 206 after establishing the exercising posture signal axis and the exercising posture verification threshold. Upon enabling rate responsive pacing, control module 206 determines activity metrics from the activity axis signal established at block 501, and determines the SIR from the activity metrics. When the SIR is determined, the control module 206 compares it to a rate threshold at block 510 prior to adjusting the pacing rate based on the SIR. If the SIR is less than the rate threshold, the rate response is allowed by adjusting the pacing rate to the SIR at block 516.

If the SIR is greater than the rate threshold, however, control module 206 determines the DC amplitude of the established exercising posture axis signal at block 512 and compares it to the exercising posture verification threshold. If the DC signal of the posture signal axis is greater than the posture verification threshold, the patient is confirmed to be in an exercising posture, e.g., an upright posture, at block 514. Control module 206 allows the pacing rate response adjustment to the SIR to be performed at block 516.

If the DC amplitude of the posture axis signal is less than the posture verification threshold ("no" branch of block 512), the control module 206 detects a non-exercising posture at block 518. In other words, the exercising posture is not verified to support an increase in pacing rate based on the SIR. Control module 206 withholds the rate response to the SIR at block 520. In this case, the established posture axis signal less than the verification threshold causes the pacing rate to be set to a rate that is not correlated to the activity metric. The pacing rate is adjusted in a manner that is correlated to the activity metric (according to the SIR transfer function) only when the exercising posture axis signal meets or exceeds the exercising posture threshold or other posture verification criteria. A high activity metric could be obtained due to increased contribution of heart motion in some patient postures that do not typically correspond to exercising patient postures and may even be a sleeping posture, resulting in a falsely high SIR. When the rate response is withheld at block 520 due to the exercising posture verification criteria not being met, the pulse generator 202 may be controlled by control module 206 to deliver pacing pulses at the lower rate (i.e., base pacing rate) in some examples.

The process returns to block 510 to continue determining activity metrics and corresponding SIRs. If the exercising posture verification criteria do become met, the pacing rate may be set according to the activity-metric based SIR.

While the process of flow charts 400 and 500 indicate a method for verifying an exercising posture based on an established exercising posture signal axis meeting a verification threshold, it is recognized that verification of a non-exercising posture may be included in some examples. A non-exercising posture signal axis may be established at block 506 in addition or alternatively to the exercising posture signal axis. For example, if the patient is known to sleep on his/her side, and elevated activity counts are observed in this known resting posture during the establishment of the activity signal axis at block 501, a resting posture signal axis may be established at block 506 as an accelerometer axis having a DC signal amplitude nearest ±1

G when the patient assumes the known resting posture. A verification threshold may be set for detecting the resting posture when the DC signal exceeds the resting posture verification threshold.

Instead of or in addition to comparing an exercising posture axis signal to a verification threshold at block 512, a resting posture axis signal may be compared to a resting posture verification threshold for detecting a non-exercising posture at block 518 when the resting posture verification threshold is reached or exceeded. If the resting posture verification threshold is not reached or exceeded, the exercising posture may be verified at block 514. One or more resting posture signal axes may be established, e.g., right-side lying, left-side lying and/or supine, along with criteria for verifying the respective resting, non-exercising posture and/or precluding verification of an exercising posture.

Figure 7:
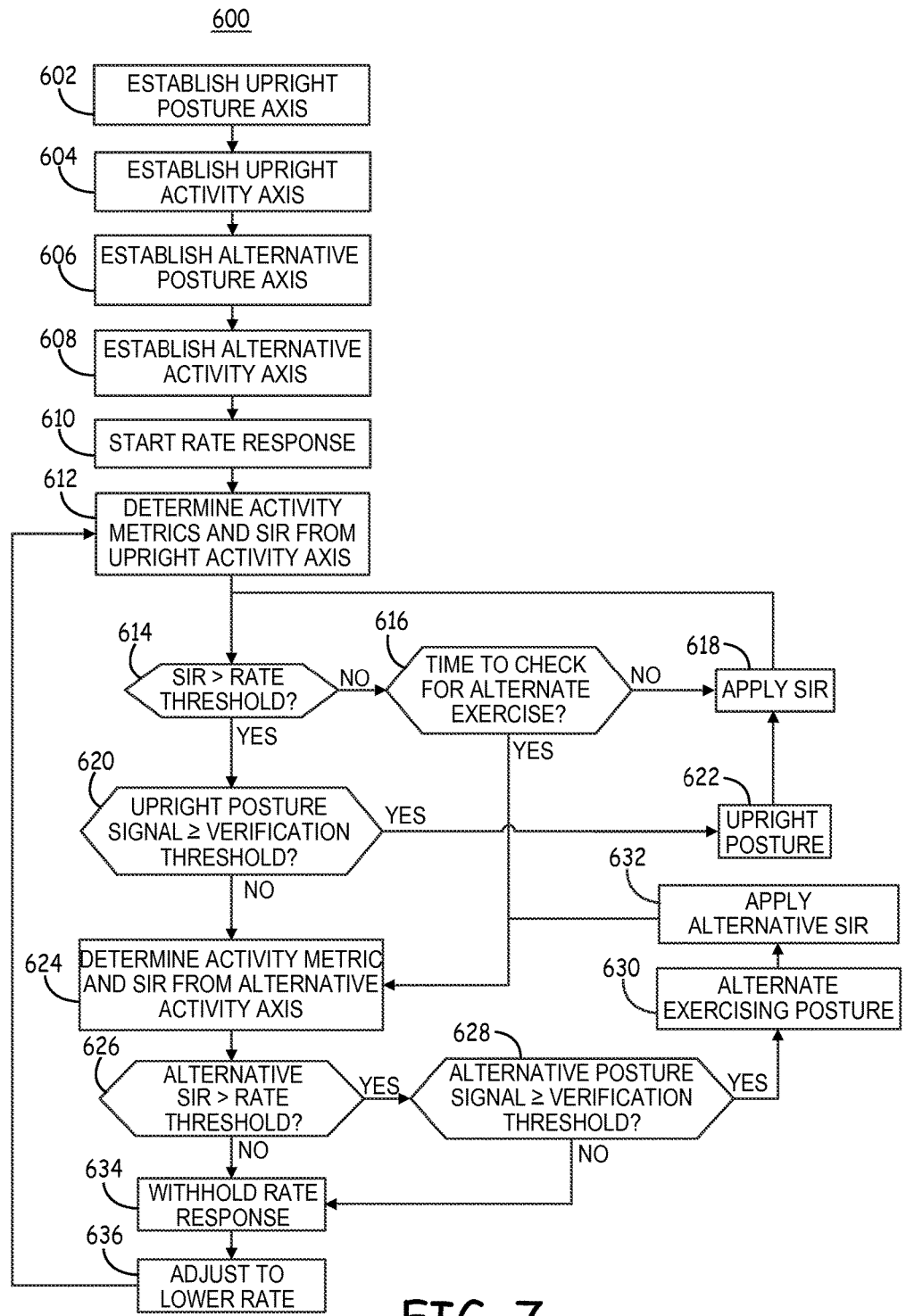
FIG. 7 is a flow chart of a method for controlling rate responsive pacing according to yet another example.

FIG. 7 is a flow chart 600 of a method for controlling rate responsive pacing according to another example. At block 602, an upright posture axis is established. An upright posture may be assumed to be the dominant patient posture during activity and exercise, when a pacing rate faster than the lower pacing rate is appropriate. The upright posture axis may be established at block 602 by asking the patient to assume an upright position, transmitting a command to the pacemaker 100 that signals that the patient is in an upright position and automatically identifying the accelerometer axis having a DC signal amplitude nearest ±1 G.

An upright activity axis is established at block 604. The upright activity axis may be established by manually or automatically comparing activity counts during rest and during upright activity for each accelerometer axis. For example, during the determination of the upright posture axis at block 602, a resting activity metric may be determined for each accelerometer axis. At block 604, the patient is instructed to perform upright exercise, e.g., walking or jogging, and control module 206 determines an exercising activity metric for each of the accelerometer axes. The axis having the greatest difference between the resting activity metric and the exercising activity metric may be identified as the upright activity axis. The upright activity axis and the upright posture axis may or may not be the same accelerometer axis.

The comparisons between the activity metrics during upright rest and upright activity for each axis and identification of the upright activity axis may be made automatically by control module 206. In another example, the resting and exercising activity metrics for each axis may be transmitted to the external device 20 for display to a user for manual comparison. The user may select the upright activity axis based on the displayed activity metric data and program the selected upright activity axis by transmitting a programming command back to pacemaker 100 using external device 20.

Some patients may perform exercise, such as swimming or cycling, in a different exercising posture, other than the upright posture. In order to provide an appropriate rate response when the patient is exercising in a non-upright posture, an alternative exercise posture axis and an alternative activity axis may be identified at blocks 606 and 608 respectively. These alternative axes may be identified in a similar manner as the upright posture and activity axes.

For example, if the patient is known to swim on an occasional or regular basis, the patient may be asked to assume a prone position, e.g., as generally used during freestyle and breaststroke. The DC signal of each accelerometer axis may be determined and the axis having a DC signal nearest to ±1 G in the prone position may be identified as the alternative exercise posture axis at block 606.

While in the prone position and at rest, an activity metric may also be determined from each accelerometer axis signal. In some cases, an exercising activity metric may be determined for each accelerometer axis while the patient is actually swimming or performing repetitive exercise in the prone position. The alternative exercise activity axis may be identified as the axis having the greatest difference between the rest and the exercising activity metrics, either automatically by control module 206 or by a user.

Alternatively, it may be assumed that forward acceleration during swimming will occur primarily along the accelerometer axis identified as the upright posture axis at block 602. In other words, when the patient is swimming, the patient's head will generally accelerate in the forward direction along an axis generally aligned with the upright posture axis. As such, the upright posture axis may automatically or manually be selected as the alternative exercise activity axis at block 608.

A posture axis and an activity axis may be identified for one or more types of activities that a given patient is known to engage in. For example, a posture axis and an activity axis may be identified for upright activity as well as swimming and cycling for a given patient such that more than one posture axis and activity axis pair for monitoring patient activity and verifying patient posture are identified and established for use in controlling rate responsive pacing in the given patient.

The posture axis and activity axis identified for upright activity and each alternative exercise may be stored in memory 210. A posture axis used for one type of activity may be the same as the posture axis used for another type of activity but the activity axis for the two types of activities may be different. In other cases, the activity axis may be the same for two different types of activity, but the posture axes could be different. In other cases, both the posture axis and the activity axis established for two different activities are different. If the posture axis and the activity axis are found to be the same for more than one type of activity, an additional alternative posture and activity axis pair need not be stored.

After establishing and storing the upright posture and activity axes and any desired alternative posture and activity axes pairs, rate responsive pacing may be enabled at block 610. At block 612, control module 206 may determine activity metrics and the correlated SIR from the upright activity axis signal, which may be used as the default patient activity monitoring axis. Most activities of daily living and many forms of exercise and exertion may be performed in an upright position so the activity axis established as the upright activity axis may be the default axis used to determine activity metrics and SIR.

If the SIR based on the upright activity axis signal is not greater than a rate threshold at block 614, as described previously in conjunction with FIG. 5, the control module 206 may determine if it is time to check for alternative exercise or activity at block 616. The pacemaker 100 may be programmed to monitor for an alternative exercise at certain time intervals, particular times of day, and/or particular days of the week. For example, the patient may be known to swim during particular hours, e.g., between 8 am and 8 pm, such that an alternative activity axis established for swimming is monitored only during those hours. Alternatively, the control module 206 may regularly determine activity metrics from the alternative exercise activity axis in parallel to monitoring the upright activity axis.

In another example, the patient may use external device 20, embodied as a handheld device or home monitor, to signal pacemaker 100 that it is time to begin monitoring for the alternative exercise. The control module 206 may monitor for the alternative exercise for a fixed period of time after receiving the signal to start monitoring for the alternative exercise. In other examples, the patient may use external device 20 to signal pacemaker 100 to stop monitoring for the alternative exercise when the exercise is complete or no longer going to be performed.

If it is not time to check for an alternate exercise, the currently determined SIR based on the activity metric (that was less than the rate threshold) determined from the upright activity axis is applied at block 618. If it is time to check for alternate exercise, the process advances to block 624 to determine an activity metric from the alternative exercise activity axis.

Referring again to decision block 614, if the SIR based on the upright activity axis signal is greater than the rate threshold, the DC signal from the upright posture axis of the accelerometer is compared to a verification threshold for verifying that the patient is in an upright posture before applying the SIR. An elevated activity metric falsely indicating increased patient activity may occur when heart motion is contributing to the accelerometer signal due to patient body position rather than due to actual patient activity. As such, if the DC signal of the upright posture axis is equal to or greater than a verification threshold, the upright posture is verified at block 622. The SIR that is greater than the rate threshold is likely caused by valid patient activity in an upright posture. The SIR determined based on the upright activity axis signal is applied at block 618. The control module 206 controls the pulse generator 202 to deliver pacing pulses at the determined SIR.

Under the conditions of an SIR determined from the upright activity axis being greater than the rate threshold but the upright posture axis signal not meeting the verification threshold at block 620, an activity metric may be determined from the alternative activity axis at block 624. The upright activity axis SIR that is greater than the rate threshold may be caused by an alternative activity when the patient is in a non-upright posture so that an increase in pacing rate may still be appropriate. As such, an activity metric and SIR may be determined from the alternative activity axis at block 624 and compared to a rate threshold at block 626. The rate threshold applied at block 626 may be the same or different than the rate threshold applied at block 614. Different transfer functions maybe used in deriving the SIR from activity metrics determined from different accelerometer axes. As such, different rate thresholds may be used.

If the SIR determined from the alternative activity axis is greater than its respective rate threshold at block 626, the DC amplitude of the alternative posture axis signal is compared to a posture verification threshold at block 628. The alternate exercising posture is detected by the control module 206 at block 630 if the alternative posture axis signal meets the verification threshold, confirming that the SIR based on the alternative exercise activity axis is valid. The alternative SIR may be used by the control module 206 to control the pacing rate delivered by pulse generator 202 at block 632.

The alternative SIR determined from the alternative activity axis signal may be used alone to control the pacing rate or a combination of the alternative SIR and the SIR determined from the upright activity axis signal may be used to control pacing rate. For example, if the SIR determined from the upright activity axis is greater than the rate threshold (block 614), the SIR from the upright activity axis may be used in combination with the alternative SIR in making a final pacing rate determination by control module 206. If the SIR determined from the upright threshold was not greater than the rate threshold at block 614, but the alternative SIR is greater than the rate threshold and the alternative exercising posture is verified (block 628), only the alternative SIR may be used by the control module 206 to set the pacing rate.

The control module 206 may continue to monitor patient activity using the alternative activity axis by returning to block 624. As long as the alternative SIR is greater than the rate threshold (block 624) and the alternative posture signal is greater than the posture verification threshold (block 628), the alternative SIR is used to control the pacing rate delivered by pulse generator 202. If the alternative SIR drops below the rate threshold, the pacing rate may be adjusted back to the lower rate at block 636, and the control module 206 may revert back to monitoring the upright activity axis signal for determining SIR at block 612. While flow chart 600 shows an adjustment back to the lower rate at block 636 before determining the activity metric and SIR from the upright activity axis, it is to be understood that after controlling the pacing rate based on the alternative SIR at block 622, control module 206 may determine the activity metric and SIR from the upright activity axis signal before adjusting the pacing rate back down to the lower rate. If a rate greater than the lower rate is indicated, the control module 206 can set the pacing rate directly to the SIR based on the upright activity axis signal (and upright posture verification) as needed. In other examples, after adjusting the pacing rate based on the alternative SIR, the control module may continue monitoring the upright activity axis signal in parallel with the alternative activity axis signal monitoring.

In other examples, the alternative activity axis signal may be monitored for a predetermined period of time for controlling rate responsive pacing according to the alternative SIR. If the time period has expired, e.g., one hour, two hours or other predetermined time interval, control module 206 may automatically revert back to checking the upright activity axis signal at block 612.

If the alternative SIR is not greater than the rate threshold at block 626, or if the DC signal of the alternative posture axis is not greater than the posture verification threshold at block 628, control module 206 withholds rate responsive pacing at the SIRs determined from both the upright activity axis and the alternative exercise activity axis at block 634. Even if the SIR of the upright activity axis is greater than a rate threshold (block 614), indicating an increased level of patient activity, the control module 206 does not provide rate responsive pacing at the SIR at either of blocks 618 or 632 unless the upright posture is verified (block 620), or the alternate posture is verified (block 628).

When an exercising posture is not verified, either upright or the alternative exercising posture, the pacing rate may be set to the lower rate at block 636. If the pacing rate is being set to the lower rate from a higher pacing rate, the pacing rate may be gradually adjusted to the lower rate to avoid sudden changes in heart rate. In other examples, the pacing rate is set to a rate less than at least one of the upright SIR or the alternative SIR to a rate that is not correlated to the activity metrics determined from at least one of the upright activity axis or the alternative activity axis.

After setting the pacing rate at one of blocks 618, 632, or 636, the control module 206 returns to block 612 to continue monitoring patient activity by determining activity metrics and SIR from the upright activity axis signal. In this way, when patient posture causes heart motion to significantly contribute to the activity signal, elevated pacing rates are avoided yet appropriate rate response is provided as needed for the patient that engages in a variety of physical activities.

Thus, various embodiments of a medical device and method have been described for controlling rate responsive pacing. However, one of ordinary skill in the art will appreciate that various modifications may be made to the described embodiments without departing from the scope of the following claims.

For example, the following Items are illustrative of further embodiments:

Item 1. A method for controlling a pacing rate by a rate responsive implantable pacemaker, comprising:
sensing an activity signal correlated to a metabolic demand of a patient;
sensing a posture signal correlated to a physical body posture of the patient;
determining a sensor indicated pacing rate from the activity signal;
comparing the posture signal to verification criteria for confirming an exercising posture of the patient; and
withholding an adjustment of a pacing rate to the sensor indicated pacing rate when the verification criteria are not met.

Item 2. The method of item 1, wherein withholding the adjustment to the sensor indicated pacing rate comprises setting the pacing rate to a rate that is not correlated to the activity signal.

Item 3. The method of any one of items 1-2, further comprising:
comparing the sensor indicated pacing rate to a rate threshold, and
comparing the posture signal to the verification threshold only when the sensor indicated pacing rate is greater than the rate threshold.

Item 4. The method of any one of items 1-3, wherein withholding the adjustment to the sensor indicated pacing rate comprises setting the pacing rate to a base pacing rate.

Item 5. The method of any one of items 1-4, wherein the activity signal and the posture signal are sensed from a multi-axis accelerometer, the method further comprising:
establishing a first axis of the multi-axis accelerometer as an activity signal axis for sensing the activity signal; and
establishing a second axis of the multi-axis accelerometer as a posture signal axis for sensing the posture signal.

Item 6. The method of item 5, wherein establishing the second axis comprises:
determining a DC signal of each axis of the multi-axis accelerometer during a known patient posture; and
selecting the posture signal axis as one of the axes of the multi-axis accelerometer having the DC signal closest to a positive or negative 1 G acceleration.

Item 7. The method of item 5, wherein establishing the first axis comprises:
determining a resting activity metric from each axis of the multi-axis accelerometer during a first patient posture while the patient is at rest;
determining an exercising activity metric from each axis of the multi-axis accelerometer during the first patient posture while the patient is exercising;
determining a difference between the resting activity metric and the exercising activity metric for each axis; and
selecting the activity signal axis as one of the axes of the multi-axis accelerometer having at least one of a lowest resting activity metric or a greatest difference between the resting activity metric and the exercising activity metric.

Item 8. The method of item 5, further comprising:
establishing the second axis of the multi-axis accelerometer by identifying an axis of the multi-axis accelerometer having a DC signal nearest to a positive or negative acceleration of 1 G when the patient is in an upright posture; and
setting the posture verification criteria based on the DC signal of the second axis that is received when the patient is in the upright posture.

Item 9. The method of any one of items 1-8, wherein the activity signal and the posture signal are sensed from a multi-axis accelerometer included in the pacemaker, the method further comprising:
establishing a first activity signal axis of the multi-axis accelerometer for monitoring patient activity corresponding to a first patient posture;
establishing a first posture signal axis of the multi-axis accelerometer for detecting the first patient posture;
establishing a second activity signal axis of the multi-axis accelerometer for monitoring patient activity corresponding to a second patient posture;
establishing a second posture signal axis of the multi-axis accelerometer for detecting the second patient posture;
determining a first sensor indicated pacing rate from the first activity signal axis;
comparing the first sensor indicated pacing rate to a first rate threshold;
in response to the first sensor indicated pacing rate being greater than the first rate threshold, comparing a signal from the first posture signal axis to first posture verification criteria;
determining a second sensor indicated pacing rate from the second activity signal axis;
comparing the second sensor indicated pacing rate to a second rate threshold;
in response to the second sensor indicated pacing rate being greater than the second rate threshold, comparing a signal from the second posture signal axis to second posture verification criteria;
setting a pacing rate based on at least one of the first sensor indicated pacing rate and the second sensor indicated pacing rate in response to at least one of the signal from the first posture signal axis meeting the first posture verification criteria and the signal from the second posture signal axis meeting the second posture verification criteria; and
setting the pacing rate to a rate that is not correlated to the first sensor indicated pacing rate and not correlated to the second sensor indicated pacing rate in response to the signal from first posture signal axis not meeting the first posture verification criteria and the signal from the second posture signal axis not meeting the second posture verification criteria.

Item 10. The method of item 9, further comprising:
comparing the second sensor indicated pacing rate to the second rate threshold in response to the first sensor indicated pacing rate being greater than the first rate threshold and the signal from the first posture signal axis not meeting the first posture verification criteria.

Item 11. An implantable rate responsive pacemaker, comprising:
a sensor module configured to produce an activity signal correlated to a metabolic demand of a patient and a posture signal correlated to patient posture;
a pulse generator configured to generate and deliver pacing pulses to a patient's heart via a pair of electrodes coupled to the pacemaker; and
a control module coupled to the pulse generator and the sensor module and configured to:

determine a sensor indicated pacing rate from the activity signal;
compare the posture signal to verification criteria for confirming an exercising posture of the patient; and
withhold an adjustment of a pacing rate to the sensor indicated pacing rate when the verification criteria are not met.

Item 12. The pacemaker of item 11, wherein the control module is further configured to withhold the adjustment to the sensor indicated pacing rate by setting the pacing rate to a rate that is not correlated to the activity signal.

Item 13. The pacemaker of any one of items 11-12, wherein the control module is further configured to:
compare the sensor indicated pacing rate to a rate threshold, and
compare the posture signal to the verification threshold only when the sensor indicated pacing rate is greater than the rate threshold.

Item 14. The pacemaker of any one of items 11-13, wherein the control module is further configured to withhold the adjustment to the sensor indicated pacing rate by setting the pacing rate to a base pacing rate.

Item 15. The pacemaker of any one of items 11-14, wherein the sensor module comprises a multi-axis accelerometer, the control module further configured to:
establish a first axis of the multi-axis accelerometer as an activity signal axis for sensing the activity signal; and
establish a second axis of the multi-axis accelerometer as a posture signal axis for sensing the posture signal.

Item 16. The pacemaker of item 15, wherein the control module is configured to establish the second axis by:
determining a DC signal of each axis of the multi-axis accelerometer during a known patient posture; and
select the posture signal axis as one of the axes of the multi-axis accelerometer having the respective DC signal closest to a positive or negative 1 G acceleration.

Item 17. The pacemaker of item 15, wherein the control module is configured to establish the first axis by:
determining a resting activity metric from each axis of the multi-axis accelerometer during a first patient posture while the patient is at rest;
determining an exercising activity metric from each axis of the multi-axis accelerometer during the first patient posture while the patient is exercising;
determining a difference between the resting activity metric and the exercising activity metric for each axis; and
selecting the activity signal axis as one of the axes of the multi-axis accelerometer having at least one of a lowest resting activity metric or a greatest difference between the resting activity metric and the exercising activity metric.

Item 18. The pacemaker of item 15, wherein the control module is further configured to:
establish the second axis of the multi-axis accelerometer by identifying an axis of the multi-axis accelerometer having a DC signal nearest to a positive or negative acceleration of 1 G when the patient is in an upright posture; and
set the posture verification criteria based on the DC signal of the second axis that is received when the patient is in the upright posture.

Item 19. The pacemaker of any one of items 11-18, wherein:
the sensor module comprises a multi-axis accelerometer; and
the control module is further configured to:
establish a first activity signal axis of the multi-axis accelerometer for monitoring patient activity corresponding to a first patient posture;
establish a first posture signal axis of the multi-axis accelerometer for detecting the first patient posture;
establish a second activity signal axis of the multi-axis accelerometer for monitoring patient activity corresponding to a second patient posture;
establish a second posture signal axis of the multi-axis accelerometer for detecting the second patient posture;
determine a first sensor indicated pacing rate from the first activity signal axis;
compare the first sensor indicated pacing rate to a first rate threshold;
in response to the first sensor indicated pacing rate being greater than the first rate threshold, compare a signal from the first posture signal axis to first posture verification criteria;
determine a second sensor indicated pacing rate from the second activity signal axis;
compare the second sensor indicated pacing rate to a second rate threshold;
in response to the second sensor indicated pacing rate being greater than the second rate threshold, compare a signal from the second posture signal axis to second posture verification criteria;
set a pacing rate based on at least one of the first sensor indicated pacing rate and the second sensor indicated pacing rate in response to at least one of the signal from the first posture signal axis meeting the first posture verification criteria and the signal from the second posture signal axis meeting the second posture verification criteria; and
set the pacing rate to a rate that is not correlated to the first sensor indicated pacing rate and not correlated to the second sensor indicated pacing rate in response to the signal from the first posture signal axis not meeting the first posture verification criteria and the signal from the second posture signal axis not meeting the second posture verification criteria.

Item 20. The pacemaker of item 19, wherein the control module is further configured to compare the second sensor indicated pacing rate to the second rate threshold in response to the first sensor indicated pacing rate being greater than the first rate threshold and the signal from the first posture signal axis not meeting the first posture verification criteria.

Item 21. The pacemaker of any one of items 11-20, further comprising a housing enclosing the sensor module, the control module and the pulse generator,
the housing carrying the electrodes coupled to the pulse generator,
the pacemaker being an intracardiac pacemaker and the electrodes being intracardiac electrodes.

Item 22. A non-transitory, computer readable storage medium storing a set of instructions that, when executed by a control module of an implantable pacemaker, cause the pacemaker to:
determine a sensor indicated pacing rate from an activity signal correlated to a metabolic demand of a patient received by the control module from a sensor module;
compare a posture signal received by the control module from the sensor module and to posture verification criteria; and
withhold an adjustment of a pacing rate to the sensor indicated pacing rate when the posture verification criteria are not met.

The invention claimed is:
1. A method for controlling a pacing rate for a rate responsive implantable pacemaker, the method comprising:
sensing an activity signal correlated to a metabolic demand of a patient;

determining a sensor indicated pacing rate (SIR) based on the activity signal;

sensing a posture signal correlated to a physical body posture of the patient;

comparing the posture signal to one or more verification criteria correlated to an exercising posture of the patient; and withholding an adjustment of the pacing rate to be the SIR in response to the one or more verification criteria not being met.

2. The method of claim 1, wherein withholding the adjustment of the pacing rate to be the SIR comprises setting the pacing rate to a rate that is not correlated to the activity signal.

3. The method of claim 1, further comprising:

comparing the SIR to a rate threshold, and comparing the posture signal to the one or more verification criteria only in response to the SIR being greater than the rate threshold.

4. The method of claim 1, wherein withholding the adjustment of the pacing rate to be the SIR comprises setting the pacing rate to a base pacing rate.

5. The method of claim 1, wherein the activity signal and the posture signal are sensed from a multi-axis accelerometer, the method further comprising:

establishing a first axis of the multi-axis accelerometer as an activity signal axis for sensing the activity signal; and establishing a second axis of the multi-axis accelerometer as a posture signal axis for sensing the posture signal.

6. The method of claim 5, wherein establishing the second axis comprises:

determining a DC signal of each axis of the multi-axis accelerometer during a known patient posture; and selecting the posture signal axis as one of the axes of the multi-axis accelerometer having the DC signal closest to a positive or negative 1 G acceleration.

7. The method of claim 5, wherein establishing the first axis comprises:

determining a resting activity metric from each axis of the multi-axis accelerometer during a first patient posture while the patient is at rest;

determining an exercising activity metric from each axis of the multi-axis accelerometer during the first patient posture while the patient is exercising;

determining a difference between the resting activity metric and the exercising activity metric for each axis; and selecting the activity signal axis as one of the axes of the multi-axis accelerometer having at least one of a lowest resting activity metric or a greatest difference between the resting activity metric and the exercising activity metric.

8. The method of claim 5, further comprising:

establishing the second axis of the multi-axis accelerometer by identifying an axis of the multi-axis accelerometer having a DC signal nearest to a positive or negative acceleration of 1 G responsive to the patient being in an upright posture; and setting the one or more verification criteria correlated to the exercising posture of the patient based on the DC signal of the second axis that is received responsive to the patient being in the upright posture.

9. The method of claim 1, wherein the activity signal and the posture signal are sensed from a multi-axis accelerometer, wherein the pacemaker includes the multi-axis accelerometer, the method further comprising:

establishing a first activity signal axis of the multi-axis accelerometer for monitoring patient activity corresponding to a first patient posture;

establishing a first posture signal axis of the multi-axis accelerometer for detecting the first patient posture;

establishing a second activity signal axis of the multi-axis accelerometer for monitoring patient activity corresponding to a second patient posture;

establishing a second posture signal axis of the multi-axis accelerometer for detecting the second patient posture;

determining a first SIR based on the first activity signal axis;

comparing the first SIR to a first rate threshold;

in response to the first SIR being greater than the first rate threshold, comparing a signal from the first posture signal axis to a first posture verification criterion of the one or more verification criteria correlated to the exercising posture of the patient;

determining a second SIR based on the second activity signal axis;

comparing the second SIR to a second rate threshold;

in response to the second SIR being greater than the second rate threshold, comparing a signal from the second posture signal axis to a second posture verification criterion of the one or more verification criteria correlated to the exercising posture of the patient;

setting the pacing rate based on one of the first SIR or the second SIR in response to one of the signal from the first posture signal axis meeting the first posture verification criterion or the signal from the second posture signal axis meeting the second posture verification criterion; and setting the pacing rate to a rate that is not correlated to the first SIR and not correlated to the second SIR in response to the signal from first posture signal axis not meeting the first posture verification criterion and the signal from the second posture signal axis not meeting the second posture verification criterion.

10. The method of claim 9, further comprising:

comparing the second SIR to the second rate threshold in response to the first SIR being greater than the first rate threshold and the signal from the first posture signal axis not meeting the first posture verification criterion.

11. An implantable rate responsive pacemaker, comprising:

a sensor module configured to produce an activity signal correlated to a metabolic demand of a patient and a posture signal correlated to patient posture;

a pulse generator configured to generate and deliver pacing pulses to a patient's heart at a pacing rate via a pair of electrodes coupled to the pacemaker; and a control module coupled to the pulse generator and the sensor module and configured to:

determine a sensor indicated pacing rate (SIR) based on the activity signal;

compare the posture signal to one or more verification criteria correlated to an exercising posture of the patient; and withhold an adjustment of the pacing rate to be the SIR in response to the one or more verification criteria not being met.

12. The pacemaker of claim 11, wherein the control module is further configured to withhold the adjustment of the pacing rate to be the sensor indicated pacing rate by setting the pacing rate to a rate that is not correlated to the activity signal.

13. The pacemaker of claim 11, wherein the control module is further configured to:
compare the SIR to a rate threshold, and
compare the posture signal to the one or more verification criteria only in response to the SIR being greater than the rate threshold.

14. The pacemaker of claim 11, wherein the control module is further configured to adjust the pacing rate to be the SIR in response to the one or more verification criteria being met.

15. The pacemaker of claim 13, wherein the control module is configured to withhold the adjustment to the sensor indicated pacing rate by setting the pacing rate to the rate threshold.

16. The pacemaker of claim 11, wherein the control module is further configured to withhold the adjustment to the sensor indicated pacing rate by setting the pacing rate to a base pacing rate.

17. The pacemaker of claim 11, wherein the sensor module comprises a multi-axis accelerometer, the control module further configured to:
establish a first axis of the multi-axis accelerometer as an activity signal axis for sensing the activity signal; and
establish a second axis of the multi-axis accelerometer as a posture signal axis for sensing the posture signal.

18. The pacemaker of claim 17, wherein the control module is configured to establish the second axis by at least:
determining a DC signal of each axis of the multi-axis accelerometer during a known patient posture; and
selecting the posture signal axis as one of the axes of the multi-axis accelerometer having the respective DC signal closest to a positive or negative 1 G acceleration.

19. The pacemaker of claim 17, wherein the control module is configured to establish the first axis by at least:
determining a resting activity metric from each axis of the multi-axis accelerometer during a first patient posture while the patient is at rest;
determining an exercising activity metric from each axis of the multi-axis accelerometer during the first patient posture while the patient is exercising;
determining a difference between the resting activity metric and the exercising activity metric for each axis; and
selecting the activity signal axis as one of the axes of the multi-axis accelerometer having at least one of a lowest resting activity metric or a greatest difference between the resting activity metric and the exercising activity metric.

20. The pacemaker of claim 17, wherein the control module is further configured to:
establish the second axis of the multi-axis accelerometer by identifying an axis of the multi-axis accelerometer having a DC signal nearest to a positive or negative acceleration of 1 G responsive to the patient being in an upright posture; and
set the one or more verification criteria based on the DC signal of the second axis that is received responsive to the patient being in the upright posture.

21. The pacemaker of claim 11, wherein:
the sensor module comprises a multi-axis accelerometer; and
the control module is further configured to:
establish a first activity signal axis of the multi-axis accelerometer for monitoring patient activity corresponding to a first patient posture;
establish a first posture signal axis of the multi-axis accelerometer for detecting the first patient posture;
establish a second activity signal axis of the multi-axis accelerometer for monitoring patient activity corresponding to a second patient posture;
establish a second posture signal axis of the multi-axis accelerometer for detecting the second patient posture;
determine a first SIR based on the first activity signal axis;
compare the first SIR to a first rate threshold;
in response to the first SIR being greater than the first rate threshold, compare a signal from the first posture signal axis to first posture verification criterion of the more or more verification criteria correlated to the exercising posture of the patient;
determine a second SIR based on the second activity signal axis;
compare the second SIR to a second rate threshold;
in response to the second SIR being greater than the second rate threshold, compare a signal from the second posture signal axis to a second posture verification criterion of the more or more verification criteria correlated to the exercising posture of the patient;
set a pacing rate based on at least one of the first SIR and the second SIR in response to at least one of the signal from the first posture signal axis meeting the first posture verification criterion and the signal from the second posture signal axis meeting the second posture verification criterion; and
set the pacing rate to a rate that is not correlated to the first SIR and not correlated to the second SIR in response to the signal from the first posture signal axis not meeting the first posture verification criterion and the signal from the second posture signal axis not meeting the second posture verification criterion.

22. The pacemaker of claim 21, wherein the control module is further configured to compare the second SIR to the second rate threshold in response to the first SIR being greater than the first rate threshold and the signal from the first posture signal axis not meeting the first posture verification criterion.

23. The pacemaker of claim 11, further comprising a housing enclosing the sensor module, the control module and the pulse generator,
the housing carrying the electrodes coupled to the pulse generator,
the pacemaker being an intracardiac pacemaker and the electrodes being intracardiac electrodes.

24. A non-transitory, computer readable storage medium storing a set of instructions that, when executed by a control module of an implantable pacemaker, cause the pacemaker to:
determine a sensor indicated pacing rate (SIR) based on an activity signal correlated to a metabolic demand of a patient received by the control module from a sensor module;
compare a posture signal received by the control module from the sensor module to one or more posture verification criteria correlated to an exercising posture of the patient; and
withhold an adjustment of a pacing rate to be the SIR in response to the one or more posture verification criteria not being met.

* * * * *